(12) United States Patent
Syvret et al.

(10) Patent No.: US 10,590,149 B2
(45) Date of Patent: Mar. 17, 2020

(54) FLUOROSILICON NITRILE COMPOUNDS

(71) Applicant: Arkema Inc., King of Prussia, PA (US)

(72) Inventors: Robert George Syvret, Allentown, PA (US); Craig Alan Polsz, Newtown, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 16/036,973

(22) Filed: Jul. 17, 2018

(65) Prior Publication Data

US 2018/0370995 A1    Dec. 27, 2018

Related U.S. Application Data

(62) Division of application No. 15/506,330, filed as application No. PCT/US2015/045599 on Aug. 18, 2015, now Pat. No. 10,155,778.

(60) Provisional application No. 62/042,292, filed on Aug. 27, 2014.

(51) Int. Cl.
*C07F 7/14* (2006.01)
*C07F 7/12* (2006.01)

(52) U.S. Cl.
CPC . *C07F 7/14* (2013.01); *C07F 7/12* (2013.01)

(58) Field of Classification Search
None
See application file for complete search history.

(56) References Cited

U.S. PATENT DOCUMENTS

| | | | | |
|---|---|---|---|---|
| 3,053,874 | A | 9/1962 | Pepe | C07F 7/12 556/415 |
| 4,730,073 | A | 3/1988 | Takago et al. | |
| 5,126,468 | A | 6/1992 | Bank | |
| 5,283,348 | A | 2/1994 | Bank | C07F 7/14 556/415 |
| 2007/0065728 | A1 | 3/2007 | Zhang et al. | |
| 2011/0266490 | A1 | 11/2011 | West et al. | |
| 2012/0315536 | A1 | 12/2012 | Bhat et al. | |

FOREIGN PATENT DOCUMENTS

| | | | |
|---|---|---|---|
| GB | 981815 | 1/1965 | |
| GB | 981815 A | * 1/1965 | ............. C07F 7/125 |

OTHER PUBLICATIONS

ISR—International application No. PCT/US 15/45599—[U.S. Appl. No. 15/506,330—Parent]—Feb. 24, 2017 (Year: 2017).*
International Search Report, International application No. PCT/US 15/45599 (Year: 2015).*
Written Opinion of the International Searching Authority; PCT/US 15/45599 (Year: 2015).*
Tianqiao Yong., et al; Journal of Power Sources, Elsevier, 254 (2014), pp. 29-32, "Organosilicon compounds containing nitrile and oligo(ethylene oxide) substituents as safe electrolytes for high-voltage lithium-ion batteries".
U.S. National Library of Medicine—National Center for Biotechnology Information; PubChem—Open Chemistry Data Base—Compound Summary for CID 14479 (3-Cyanopropyl)methyldichlorosilane Modified Date Aug. 5, 2015; Create Date Mar. 27, 2005; 13 Pages.
U.S. National Library of Medicine—National Center for Biotechnology Information; PubChem—Open Chemistry Data Base—Compound Summary for CID 22079074 AGN-PC-03JZO2 Nov. 5, 2014; pp. 1-11.
U.S. National Library of Medicine—National Center for Biotechnology Information; PubChem—Open Chemistry Data Base—Compound Summary for CID 57848168 AGN-PC-0BYK7O Nov. 5, 2014; pp. 1-11.
U.S. National Library of Medicine—National Center for Biotechnology Information; PubChem—Open Chemistry Data Base—Compound Summary for CID 4589186 3-trimethylsilyloxypropanenitrile Nov. 5, 2014; pp. 1-12.

* cited by examiner

*Primary Examiner* — Clinton A Brooks
*Assistant Examiner* — Kofi Adzamli
(74) *Attorney, Agent, or Firm* — Steven D. Boyd

(57) ABSTRACT

Novel fluorosilicon nitrile compounds, and methods of preparing them, are described. The fluorosilicon nitrile compounds are characterized by having a total of four substituents attached to a silicon atom, wherein one or two of the substituents are fluorine atoms, one or two of the substituents are cyanoalkyl groups, which are the same as or different from each other, and the remainder of the substituents, if any, are alkyl groups, which are the same as or different from each other.

3 Claims, No Drawings

FLUOROSILICON NITRILE COMPOUNDS

This present application is the divisional of prior U.S. application Ser. No. 15/506,330 filed Feb. 24, 2017 which was a national phase under 35 USC § 371 of prior PCT International Application Number PCT/US2015/045599 filed Aug. 18, 2015 which designated the United States of America and claimed priority to U.S. Provisional Patent Application Ser. No. 62/042,292 filed Aug. 27, 2014.

FIELD OF THE INVENTION

The present invention pertains to novel fluorosilicon nitrile compounds and methods for their preparation.

DISCUSSION OF THE RELATED ART

Fluorosilicon nitrite compounds containing one or two fluorine atoms attached to a silicon atom as well as at least one cyanoalkyl group attached to the silicon atom may be used in applications such as battery fabrication (as solvents or additives, for example), semiconductor deposition, fluorosilicone glass formation, and semiconductor etching agents. The synthesis of new fluorosilicon compounds of this type would therefore be of great interest, since such new compounds may have unique and varied properties as compared to known fluorosilicon nitrile compounds.

BRIEF SUMMARY OF THE INVENTION

One aspect of the present invention provides novel fluorosilicon nitrile compounds, wherein the fluorosilicon nitrile compound has a total of four substituents attached to a silicon atom and wherein one or two of the substituents are fluorine atoms, one or two of the substituents are cyanoalkyl groups, which are the same as or different from each other (when two cyanoalkyl groups are present), and the remainder of the four substituents, if any, are alkyl groups, which are the same as or different from each other (when two alkyl groups are present); subject to the proviso that the fluorosilicon nitrile compound is not $SiF_2(CH_3)(CH_2CH_2CH(CN)CH_3)$; $SiF_2(CH_3)(CH_2CH_2CH_2CN)$; $SiF_2(CH_3)(CH_2CH(CH_3)CH_2CN)$; or $SiF_2[CH_2CH(CH_3)CH_2CN]_2$.

Also provided by the present invention are fluorosilicon nitrile compounds of general formula $Si(R^1)(R^2)(R^3)(R^4)$, wherein one or two of $R^1$-$R^4$ are fluorine atoms, one or two of $R^1$-$R^4$ are cyanoalkyl groups, which are the same as or different from each other where two cyanoalkyl groups are present, and the remaining $R^1$-$R^4$, if any, are alkyl groups; subject to the proviso that the fluorosilicon nitrile compound is not $SiF_2(CH_3)(CH_2CH_2CH(CN)CH_3)$; $SiF_2(CH_3)(CH_2CH_2CH_2CN)$; $SiF_2(CH_3)(CH_2CH(CH_3)CH_2CN)$; or $SiF_2[CH_2CH(CH_3)CH_2CN]_2$.

In another aspect of the invention, a method of making a fluorosilicon nitrile compound in accordance with the foregoing description is provided, wherein the method comprises reacting a chlorosilicon nitrile compound, the chlorosilicon nitrile compound having a total of four substituents attached to a silicon atom, wherein one or two of the substituents are chlorine atoms, one or two of the substituents are cyanoalkyl groups, which may be the same as or different from each other, and the remainder of the substituents, if any, are alkyl groups, which are the same as or different from each other, with a fluorinating agent under conditions effective to exchange fluorine atoms for the chlorine atom(s) in the chlorosilicon nitrile compound.

Still another aspect of the invention provides a method of making a fluorosilicon nitrite compound in accordance with the foregoing description, wherein the method comprises hydrosilylation of an alkene, especially a cyanoalkene, with a fluoroalkylsilane.

DETAILED DESCRIPTION OF CERTAIN EMBODIMENTS OF THE INVENTION

A fluorosilicon nitrite compound in accordance with the present invention has a total of four substituents attached to a silicon atom, wherein one or two of the substituents are fluorine atoms, one or two of the substituents are cyanoalkyl groups, which are the same as or different from each other, and the remainder of the substituents, if any, are alkyl groups, which are the same as or different from each other. However, the following fluorosilicon nitrile compounds, which are known compounds, are not considered to be within the scope of the present invention: $SiF_2(CH_3)(CH_2CH_2CH(CN)CH_3)$; $SiF_2(CH_3)(CH_2CH_2CH_2CN)$; $SiF_2(CH_3)(CH_2CH(CH_3)CH_2CN)$; and $SiF_2[CH_2CH(CH_3)CH_2CN]_2$.

In one embodiment of the invention, one substituent attached to the silicon atom is a fluorine atom, one substituent is a cyanoalkyl group, and two substituents are alkyl groups, which are the same as or different from each other.

In another embodiment of the invention, two substituents attached to the silicon atom are fluorine atoms, one substituent is a cyanoalkyl group, and one substituent is an alkyl group.

According to another embodiment, one substituent attached to the silicon atom is a fluorine atom, two substituents are cyanoalkyl groups, which are the same as or different from each other, and one substituent is an alkyl group.

In still another embodiment of the invention, two substituents attached to the silicon atom are fluorine atoms and two substituents are cyanoalkyl groups, which are the same as or different from each other.

The cyanoalkyl group or groups attached to the silicon atom may be C2-C9 cyanoalkyl groups, in one aspect of the invention. If two cyanoalkyl groups are present, they may be the same as or different from each other. The alkyl radical bearing one or more cyano (—CN) groups in the cyanoalkyl group may be a straight chain, branched, or alicyclic-containing alkyl radical. Each cyanoalkyl group may contain one, two or more cyano groups per cyanoalkyl group. Each cyano group may be substituted, for example, at a terminal position of an alkyl radical or at an internal position of an alkyl radical. For example, where the alkyl radical is a straight chain C4 alkyl radical, a cyano group may be substituted at the terminal position to provide the cyanoalkyl group —$CH_2CH_2CH_2CH_2CN$ or at an internal position to provide one of the following cyanoalkyl groups: —$CH(CN)CH_2CH_2CH_3$; —$CH_2CH(CN)CH_2CH_3$; —$CH_2CH_2CH(CN)CH_3$.

Suitable cyanoalkyl groups may, for example, be selected from the group consisting of:
- —$CH_2CH(CN)CH_3$;
- —$CH(CN)CH_2CH_3$;
- —$C(CN)(CH_3)_2$;
- —$CH_2CH_2CN$;
- —$CH(CN)CH_3$;
- —$CH_2CH_2CH(CN)CH_3$;
- —$CH_2CH(CN)CH_2CH_3$;
- —$(CH_2)_3CN$;
- —$(CH_2)_2CN$;

—(CH$_2$)$_4$CN;
—(CH$_2$)$_5$CN;
—(CH$_2$)$_3$C(CH$_3$)$_2$CN;
—CH(CH$_3$)CH$_2$CN;
—CH(CN)CH(CN)CH$_3$;
—C(CN)(CH$_3$)CH$_2$CN;
—CH(CH$_2$CN)$_2$;
—CH(CN)CH$_2$CH$_2$CN;
—CH(CH$_3$)CH(CN)$_2$;
—C(CN)$_2$(CH$_2$CH$_3$);
—CH$_2$CH(CN)CH$_2$CN;
—C(CN)(CH$_3$)CH$_2$CN;
—CH(CH$_2$CH$_3$)CH$_2$CN;
—CH(CN)CH$_2$CH$_2$CH$_3$;
—CH(CH$_3$)CH$_2$CH$_2$CN;
—CH(CH$_2$CN)CH$_2$CH$_3$;
—CH(CH$_3$)CH(CH)CH$_3$;
—C(CN)(CH$_3$)CH$_2$CH$_3$;
—CH$_2$CH(CN)CH$_2$CH$_3$;
—CH$_2$CH(CH$_3$)CH$_2$CN;
—C(CH$_3$)$_2$CH$_2$CN;
—CH(CN)CH(CH$_3$)$_2$;
—CH$_2$CH$_2$CH(CN)CH$_3$;
—CH$_2$CH(CH$_2$CN)CH$_2$CH$_3$;
—C(CH$_3$)(CH$_2$CH$_3$)CH$_2$CN;
—CH$_2$CH$_2$CH(CN)CH$_2$CH$_3$;
—CH(CH$_3$)CH(CN)CH$_2$CH$_3$;
—CH$_2$CH$_2$CH$_2$CH(CN)CH$_3$;
—CH(CH$_3$)CH$_2$CH(CN)CH$_3$;
—C(CH$_2$CH$_3$)$_2$(CN);
—CH$_2$CH$_2$CH(CH$_3$)CH$_2$CN;
—CH(CH$_3$)CH(CH$_3$)CH$_2$CN;
—(CH$_2$)$_2$C(CH$_3$)$_2$CN;
—CH(CH$_3$)C(CH$_3$)$_2$CN;
—CH(CH$_2$CH$_3$)CH(CN)CH$_3$;
—CH$_2$CH(CH$_3$)CH$_2$CH$_2$CN;
—C(CH$_3$)$_2$CH$_2$CH$_2$CN;
—CH(CH$_2$CH$_3$)CH$_2$CH$_2$CN;
—CH(CH$_2$CN)CH$_2$CH$_2$CH$_3$;
—CH(CN)CH$_2$CH$_2$CH$_2$CH$_3$;
—CH(CH$_3$)CH$_2$CH$_2$CH$_2$CN;
—C(CH$_3$)$_2$CH(CN)CH$_3$;
—C(CH$_3$)(CN)CH(CH$_3$)$_2$;
—CH(CH$_2$CN)CH(CH$_3$)$_2$;
—CH$_2$CH(CN)CH$_2$CH$_2$CH$_3$;
—C(CH$_3$)(CN)CH$_2$CH$_2$CH$_3$;
—CH$_2$CH(CN)CH(CH$_3$)$_2$;
—CH(CN)CH$_2$CH$_2$CH$_2$CH$_3$;
—CH$_2$CH(CH$_3$)CH(CN)CH$_3$;
—CH(CN)CH$_2$CH(CH$_3$)$_2$;
—CH(CN)CH(CH$_3$)CH$_2$CH$_3$;
—C(CH$_3$)(CN)CH(CN)CH$_2$CH$_3$;
—C(CN)(CH$_2$CH$_3$)CH(CN)CH$_3$;
—CH(CH$_2$CN)CH$_2$CH$_2$CH$_2$CN;
—CH(CN)CH$_2$CH$_2$CH$_2$CH$_2$CN;
—CH$_2$CH(CN)CH$_2$CH$_2$CH$_2$CN;
—C(CH$_3$)(CN)CH$_2$CH$_2$CH$_2$CN;
—C(CH$_3$)(CH$_2$CH$_3$)CH(CN)$_2$;
—C(CN)$_2$CH(CH$_3$)CH$_2$CH$_3$;
—C(CN)$_2$CH$_2$CH(CH$_3$)$_2$;
—CH(CH(CN)$_2$)CH(CH$_3$)$_2$;
—C(CN)(CH$_2$CH$_3$)CH$_2$CH$_2$CN;
—CH(CH$_3$)CH(CN)CH$_2$CH$_2$CN;
—CH$_2$CH(CN)CH$_2$CH(CN)CH$_3$;
—C(CN)(CH$_3$)CH$_2$CH(CN)CH$_3$;
—(CH$_2$)$_3$CH(CN)CH$_2$CN;
—CH(CH$_3$)CH$_2$CH(CN)CH$_2$CN;

—CH(CH$_2$CH$_3$)CH(CN)CH$_2$CN;
—C(CN)(CH$_2$CN)CH$_2$CH$_2$CH$_3$;
—C(CH$_3$)$_2$CH(CN)CH$_2$CN;
—C(CN)(CH$_2$CN)CH(CH$_3$)$_2$;
—C(CH$_3$)(CH$_2$CN)CH$_2$CH$_2$CN;
—CH(CH$_2$CN)CH(CH$_3$)CH$_2$CN;
—CH$_2$CH(CH$_2$CN)CH$_2$CH$_2$CN;
—CH$_2$CH(CH$_2$CN)CH(CN)CH$_3$;
—C(CH$_3$)(CH$_2$CN)CH(CN)CH$_3$;
—CH(CH(CN)$_2$)CH$_2$CH$_2$CH$_3$;
—C(CN)$_2$CH$_2$CH$_2$CH$_2$CH$_3$;
—CH(CH$_2$CN)CH$_2$CH(CN)CH$_3$;
—CH(CH$_2$CH$_3$)CH$_2$CH(CN)CH$_3$;
—CH(CH$_3$)CH$_2$CH$_2$CH(CN)$_2$;
—CH(CH$_2$CH$_3$)CH$_2$CH(CN)$_2$;
—CH$_2$CH(CH$_3$)CH$_2$CH(CN)$_2$;
—C(CH$_3$)$_2$CH$_2$CH(CN)$_2$;
—CH$_2$CH$_2$CH$_2$C(CN)$_2$CH$_3$;
—CH(CH$_3$)CH$_2$C(CN)$_2$CH$_3$;
—CH(CH(CN)$_2$)CH(CH$_3$)$_2$;
—CH$_2$CH$_2$CH(CH$_3$)CH(CN)$_2$;
—CH(CH$_3$)CH(CH$_3$)CH(CN)$_2$; and
—CH$_2$CH$_2$CH$_2$CH$_2$CH(CN)$_2$ and combinations thereof,
where the fluorosilicon nitrile compound contains two cyanoalkyl groups per molecule.

When at least one alkyl group is present in the fluorosilicon nitrile compound as a substituent attached to the silicon atom, the alkyl group may, for example, be a C1-C8 alkyl group. The alkyl group may be straight chain or branched or may contain a cyclic structure (i.e., the alkyl group may be alicyclic). If two alkyl groups are attached to the silicon atom, they may be the same as each other or different from each other. Suitable alkyl groups include, for example, methyl, ethyl, n-propyl, iso-propyl, n-butyl, sec-butyl, iso-butyl, tert-butyl, n-pentyl and isomers thereof, n-hexyl and isomers thereof, n-heptyl and isomers thereof, and n-octyl and isomers thereof.

In one aspect of the invention, the fluorosilicon nitrile compound contains, as substituents attached to the silicon atom, one fluorine atom, one cyanoalkyl group, and two C1-C8 alkyl groups, which are the same as or different from each other. In another aspect of the invention, the fluorosilicon nitrile compound contains, as substituents attached to the silicon atom, two fluorine atoms, one cyanoalkyl group and one C1-C8 alkyl group. In these embodiments, the C1-C8 alkyl groups may, for example, be selected from the group consisting of methyl, ethyl, n-propyl, iso-propyl, n-butyl, sec-butyl, iso-butyl, tert-butyl and combinations thereof.

A further embodiment of the invention provides a fluorosilicon nitrile compound of general formula $Si(R^1)(R^2)(R^3)(R^4)$, wherein one or two of $R^1$-$R^4$ are fluorine atoms, one or two of $R^1$-$R^4$ are cyanoalkyl groups, which are the same as or different from each other where two cyanoalkyl groups are present, and the remaining $R^1$-$R^4$, if any, are alkyl groups; subject to the proviso that the fluorosilicon nitrile compound is not $SiF_2(CH_3)(CH_2CH_2CH(CN)CH_3)$; $SiF_2(CH_3)(CH_2CH_2CH_2CN)$; $SiF_2(CH_3)(CH_2CH(CH_3)CH_2CN)$; or $SiF_2[CH_2CH(CH_3)CH_2CN]_2$. The alkyl groups and cyanoalkyl groups may be any of such groups described previously.

For example, $R^1$ and $R^2$ may both be F, $R^3$ may be an alkyl group and $R^4$ may be a cyanoalkyl group. Alternatively, $R^1$ and $R^2$ may both be F and $R^3$ and $R^4$ may both be cyanoalkyl groups. In yet another aspect, R1 may be F, $R^2$ and $R^3$ may both be alkyl, and $R^4$ may be cyanoalkyl. Additionally, in a further aspect of the invention, $R^1$ may be F, $R^2$ may be alkyl, and $R^3$ and $R^4$ may both be cyanoalkyl.

Examples of fluorosilicon nitrile compounds in accordance with the present invention are shown in Table I. Each of these compounds may be synthesized from known chlorosilicon nitrile compounds containing Cl atoms, rather than F atoms, substituted on the silicon atom, using the fluorination methods described elsewhere herein.

TABLE I

| Compound # | Structure | Empirical Formula |
|---|---|---|
| 1 | [F-Si(CH3)-CH2CH(CN)(CH3)] | $C_6H_{12}NSiF$ |
| 2 | [F2-Si(CH3)-CH2CH(CN)(CH3)] | $C_5H_9NSiF_2$ |
| 3 | [F2-Si(CH3)-C(CN)(CH3)2] | $C_5H_9NSiF_2$ |
| 4 | [F2-Si(CH2CH3)-CH2CH2CN] | $C_5H_9NSiF_2$ |
| 5 | [F2-Si(CH2CH3)-CH(CN)(CH3)] | $C_5H_9NSiF_2$ |
| 6 | [F-Si(CH3)(CH3)-CH2CH2CH(CN)(CH3)] | $C_7H_{14}NSiF$ |
| 7 | [F-Si(CH3)(CH2CH3)-(CH2)3CN] | $C_7H_{14}NSiF$ |
| 8 | [F-Si(CH2CH3)(CH3CH2)-CH2CH2CN] | $C_7H_{14}NSiF$ |
| 9 | [F2-Si((CH2)3CN)2] | $C_8H_{12}N_2SiF_2$ |

TABLE I-continued

| Compound # | Structure | Empirical Formula |
|---|---|---|
| 10 | [F-Si(CH3)(CH3)-CH(CN)-CH(CN)(CH3)] | $C_7H_{11}N_2SiF$ |
| 11 | [F-Si(CH3)-((CH2)2CN)2] | $C_7H_{11}N_2SiF$ |
| 12 | [F2-Si-((CH2)2CN)2] | $C_6H_8N_2SiF_2$ |
| 13 | [F-Si(CH3)(CH3)-(CH2)3C(CN)(CH3)2] | $C_9H_{18}NSiF$ |
| 14 | [F2-Si-((CH2)3CH3)((CH2)3CN)] | $C_8H_{15}NSiF_2$ |
| 15 | [F-Si(CH3)(CH(CH3)2)-(CH2)3CN ... H3C-CH-Si] | $C_{10}H_{20}NSiF$ |
| 16 | [F2-Si(CH2CH3)-(CH2)3CN] | $C_6H_{11}NSiF_2$ |

Additional exemplary fluorosilicon nitrile compounds illustrative of the present invention are shown in Table II. These compounds contain one or two fluorine atoms attached to a silicon atom, a cyanoalkyl group attached to the silicon atom, and one or two methyl groups attached to the silicon atom. Also within the scope of the present invention are fluorosilicon compounds homologous or analogous to those shown in Table II in which the methyl group (in the case of the difluoromethylsilicon nitriles) or one or both of the methyl groups (in the case of the fluorodimethylsilicon nitriles) is or are substituted by an alkyl group other than methyl, in particular a branched or straight chain C2-C8 alkyl group such as ethyl, n-propyl, iso-propyl, n-butyl, sec-butyl, iso-butyl, tert-butyl and the like.

TABLE II

| Compound # | Fluorodimethylsilicon Nitrile | Difluoromethylsilicon Nitrile |
|---|---|---|
| 21 | 21a = $C_6H_{12}NSiF$ | 21b = $C_5H_9NSiF_2$ |
|  | 21c = $C_6H_{12}NSiF$ | 21d = $C_5H_9NSiF_2$ |
| 22 | 22a = $C_7H_{11}N_2SiF$ | 22b = $C_6H_8N_2SiF_2$ |
|  | 22c = $C_7H_{11}N_2SiF$ | 22d = $C_6H_8N_2SiF_2$ |
| 23 | 23a = $C_7H_{11}N_2SiF$ | 23b = $C_6H_8N_2SiF_2$ |
|  | 23c = $C_7H_{11}N_2SiF$ | 23d = $C_6H_8N_2SiF_2$ |
| 24 | 24a = $C_7H_{11}N_2SiF$ | 24b = $C_6H_8N_2SiF_2$ |
|  | 24c = $C_7H_{11}N_2SiF$ | 24d = $C_6H_8N_2SiF_2$ |

TABLE II-continued

| Compound # | Fluorodimethylsilicon Nitrile | Difluoromethylsilicon Nitrile |
|---|---|---|
| 25 | 25a = $C_7H_{11}N_2SiF$ | 25b = $C_6H_8N_2SiF_2$ |
|  | 25c = $C_7H_{11}N_2SiF$ | 25d = $C_6H_8N_2SiF_2$ |
| 26 | 26a = $C_7H_{14}NSiF$ | 26b = $C_6H_{11}NSiF_2$ |
|  | 26c = $C_7H_{14}NSiF$ | 26d = $C_6H_{11}NSiF_2$ |
| 27 | 27a = $C_7H_{14}NSiF$ | 27b = $C_6H_{11}NSiF_2$ |
|  | 27c = $C_7H_{14}NSiF$ | 27d = $C_6H_{11}NSiF_2$ |
| 28 | 28a = $C_7H_{14}NSiF$ | 28b = $C_6H_{11}NSiF_2$ |
|  | 28c = $C_7H_{14}NSiF$ | 28d = $C_6H_{11}NSiF_2$ |

TABLE II-continued

| Compound # | Fluorodimethylsilicon Nitrile | Difluoromethylsilicon Nitrile |
|---|---|---|
| 29 | 29a = $C_7H_{14}NSiF$ | 29b = $C_6H_{11}NSiF_2$ |
|  | 29c = $C_7H_{14}NSiF$ | 29d = $C_6H_{11}NSiF_2$ |
| 30 | 30a = $C_7H_{14}NSiF$ | 30b = $C_6H_{11}NSiF_2$ |
| 31 | 31a = $C_7H_{14}NSiF$ |  |
|  | 31b = $C_7H_{14}NSiF$ | 31c = $C_6H_{11}NSiF_2$ |
| 32 | 32a = $C_7H_{14}NSiF$ | 32b = $C_6H_{11}NSiF_2$ |
| 33 | 33 = $C_7H_{14}NSiF$ |  |
| 34 | 34a = $C_8H_{16}NSiF$ | 34b = $C_7H_{13}NSiF_2$ |

TABLE II-continued

| Compound # | Fluorodimethylsilicon Nitrile | Difluoromethylsilicon Nitrile |
|---|---|---|
|  | 34c = $C_8H_{16}NSiF$ | 34d = $C_7H_{13}NSiF_2$ |
| 35 | 35a = $C_8H_{16}NSiF$ | 35b = $C_7H_{13}NSiF_2$ |
|  | 35c = $C_8H_{16}NSiF$ | 35d = $C_7H_{13}NSiF_2$ |
| 36 | 36a = $C_8H_{16}NSiF$ | 36b = $C_7H_{13}NSiF_2$ |
|  | 36c = $C_8H_{16}NSiF$ | 36d = $C_7H_{13}NSiF_2$ |
| 37 | 37a = $C_8H_{16}NSiF$ | 37b = $C_7H_{13}NSiF_2$ |
| 38 | 38a = $C_8H_{16}NSiF$ | 38b = $C_7H_{13}NSiF_2$ |

TABLE II-continued

| Compound # | Fluorodimethylsilicon Nitrile | Difluoromethylsilicon Nitrile |
|---|---|---|
| | 38c = $C_8H_{16}NSiF$ | 38d = $C_7H_{13}NSiF_2$ |
| 39 | 39a = $C_8H_{16}NSiF$ | 39b = $C_7H_{13}NSiF_2$ |
| | 39c = $C_8H_{16}NSiF$ | 39d = $C_7H_{13}NSiF_2$ |
| 40 | 40a = $C_8H_{16}NSiF$ | 40b = $C_7H_{13}NSiF_2$ |
| 41 | 41a = $C_8H_{16}NSiF$ | 41b = $C_7H_{13}NSiF_2$ |
| | 41c = $C_8H_{16}NSiF$ | 41d = $C_7H_{13}NSiF_2$ |
| 42 | 42a = $C_8H_{16}NSiF$ | 42b = $C_7H_{13}NSiF_2$ |

TABLE II-continued

| Compound # | Fluorodimethylsilicon Nitrile | Difluoromethylsilicon Nitrile |
|---|---|---|
| | 42c = $C_8H_{16}NSiF$ (structure: $H_3C$–Si(F)(CH$_3$)–CH(CH$_2$CH$_2$CH$_3$)–CH$_2$CN) | 42d = $C_7H_{13}NSiF_2$ (structure: F–Si(F)(CH$_3$)–CH(CH$_2$CH$_2$CH$_3$)–CH$_2$CN) |
| 43 | 43a = $C_8H_{16}NSiF$ (structure: $H_3C$–Si(F)(CH$_3$)–CH((CH$_2$)$_3$CH$_3$)–CN) | 43b = $C_7H_{13}NSiF_2$ (structure: F–Si(F)(CH$_3$)–CH((CH$_2$)$_3$CH$_3$)–CN) |
| 44 | 44a = $C_8H_{16}NSiF$ (structure: $H_3C$–Si(F)(CH$_3$)–(CH$_2$)$_5$CN) | 44b = $C_7H_{13}NSiF_2$ (structure: F–Si(F)(CH$_3$)–(CH$_2$)$_5$CN) |
| | 44c = $C_8H_{16}NSiF$ (structure: $H_3C$–Si(F)(CH$_3$)–CH(CH$_3$)–(CH$_2$)$_3$CN) | 44d = $C_7H_{13}NSiF_2$ (structure: F–Si(F)(CH$_3$)–CH(CH$_3$)–(CH$_2$)$_3$CN) |
| 45 | 45a = $C_8H_{16}NSiF$ (structure: $H_3C$–Si(F)(CH$_3$)–C(CH$_3$)(CH$_3$)–CH(CH$_3$)–CN) | 45b = $C_7H_{13}NSiF_2$ (structure: F–Si(F)(CH$_3$)–C(CH$_3$)(CH$_3$)–CH(CH$_3$)–CN) |
| | 45c = $C_8H_{16}NSiF$ | 45d = $C_7H_{13}NSiF_2$ |
| 46 | 46a = $C_8H_{16}NSiF$ (structure: $H_3C$–Si(F)(CH$_3$)–CH(CH$_2$CN)–CH(CH$_3$)–CH$_3$) | 46b = $C_7H_{13}NSiF_2$ (structure: F–Si(F)(CH$_3$)–CH(CH$_2$CN)–CH(CH$_3$)–CH$_3$) |
| 47 | 47a = $C_8H_{16}NSiF$ (structure: $H_3C$–Si(F)(CH$_3$)–CH$_2$CH(CN)–CH$_2$CH$_2$CH$_3$) | 47b = $C_7H_{13}NSiF_2$ (structure: F–Si(F)(CH$_3$)–CH$_2$CH(CN)–CH$_2$CH$_2$CH$_3$) |

TABLE II-continued

| Compound # | Fluorodimethylsilicon Nitrile | Difluoromethylsilicon Nitrile |
|---|---|---|
| | 47c = $C_8H_{16}NSiF$ | 47d = $C_7H_{13}NSiF_2$ |
| 48 | 48a = $C_8H_{16}NSiF$ | 48b = $C_7H_{13}NSiF_2$ |
| 49 | 49a = $C_8H_{16}NSiF$ | 49b = $C_7H_{13}NSiF_2$ |
| 50 | 50a = $C_8H_{16}NSiF$ | 50b = $C_7H_{13}NSiF_2$ |
| 51 | 51a = $C_8H_{16}NSiF$ | 51b = $C_7H_{13}NSiF_2$ |
| 52 | 52a = $C_8H_{16}NSiF$ | 52b = $C_7H_{13}NSiF_2$ |
| 53 | 53a = $C_9H_{15}N_2SiF$ | 53b = $C_8H_{12}N_2SiF_2$ |

TABLE II-continued

| Compound # | Fluorodimethylsilicon Nitrile | Difluoromethylsilicon Nitrile |
|---|---|---|
| | 53c = C₉H₁₅N₂SiF | 53d = C₈H₁₂N₂SiF₂ |
| 54 | 54a = C₉H₁₅N₂SiF | 54b = C₈H₁₂N₂SiF₂ |
| | 54c = C₉H₁₅N₂SiF | 54d = C₈H₁₂N₂SiF₂ |
| 55 | 55a = C₉H₁₅N₂SiF | 55b = C₈H₁₂N₂SiF₂ |
| | 55c = C₉H₁₅N₂SiF | 55d = C₈H₁₂N₂SiF₂ |
| 56 | 56a = C₉H₁₅N₂SiF | 56b = C₈H₁₂N₂SiF₂ |
| | 56c = C₉H₁₅N₂SiF | 56d = C₈H₁₂N₂SiF₂ |

TABLE II-continued

| Compound # | Fluorodimethylsilicon Nitrile | Difluoromethylsilicon Nitrile |
|---|---|---|
| 57 | 57a = C$_9$H$_{15}$N$_2$SiF | 57b = C$_8$H$_{12}$N$_2$SiF$_2$ |
|  | 57c = C$_9$H$_{15}$N$_2$SiF | 57d = C$_8$H$_{12}$N$_2$SiF$_2$ |
| 58 | 58a = C$_9$H$_{15}$N$_2$SiF | 58b = C$_8$H$_{12}$N$_2$SiF$_2$ |
|  | 58c = C$_9$H$_{15}$N$_2$SiF | 58d = C$_8$H$_{12}$N$_2$SiF$_2$ |
| 59 | 59a = C$_9$H$_{15}$N$_2$SiF | 59b = C$_8$H$_{12}$N$_2$SiF$_2$ |
|  | 59c = C$_9$H$_{15}$N$_2$SiF | 59d = C$_8$H$_{12}$N$_2$SiF$_2$ |
| 60 | 60a = C$_9$H$_{15}$N$_2$SiF | 60b = C$_8$H$_{12}$N$_2$SiF$_2$ |

TABLE II-continued

| Compound # | Fluorodimethylsilicon Nitrile | Difluoromethylsilicon Nitrile |
|---|---|---|
| | 60c = $C_9H_{15}N_2SiF$ | 60d = $C_8H_{12}N_2SiF_2$ |
| 61 | 61a = $C_9H_{15}N_2SiF$ | 61b = $C_8H_{12}N_2SiF_2$ |
| 62 | 62a = $C_9H_{15}N_2SiF$ | 62b = $C_8H_{12}N_2SiF_2$ |
| 63 | 63a = $C_9H_{15}N_2SiF$ | 63b = $C_8H_{12}N_2SiF_2$ |
| | 63c = $C_9H_{15}N_2SiF$ | 63d = $C_8H_{12}N_2SiF_2$ |
| 64 | 64a = $C_9H_{15}N_2SiF$ | 64b = $C_8H_{12}N_2SiF_2$ |
| | 64c = $C_9H_{15}N_2SiF$ | 64d = $C_8H_{12}N_2SiF_2$ |

TABLE II-continued

| Compound # | Fluorodimethylsilicon Nitrile | Difluoromethylsilicon Nitrile |
|---|---|---|
| 65 | 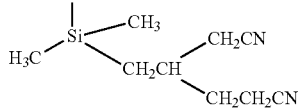<br>65a = C$_9$H$_{15}$N$_2$SiF | 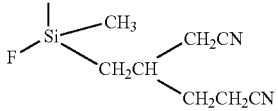<br>65b = C$_8$H$_{12}$N$_2$SiF$_2$ |
| 66 | 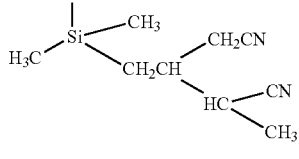<br>66a = C$_9$H$_{15}$N$_2$SiF | 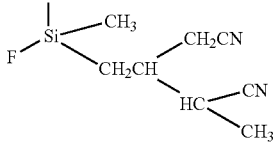<br>66b = C$_8$H$_{12}$N$_2$SiF$_2$ |
|  | 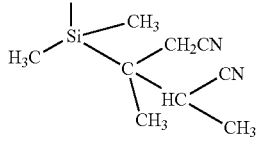<br>66c = C$_9$H$_{15}$N$_2$SiF | 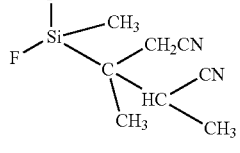<br>66d = C$_8$H$_{12}$N$_2$SiF$_2$ |
| 67 | 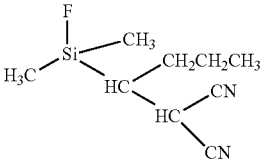<br>67a = C$_9$H$_{15}$N$_2$SiF | 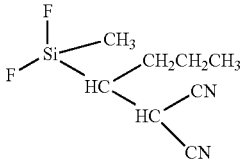<br>67b = C$_8$H$_{12}$N$_2$SiF$_2$ |
|  | 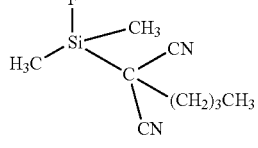<br>67c = C$_9$H$_{15}$N$_2$SiF | 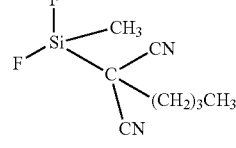<br>67d = C$_8$H$_{12}$N$_2$SiF$_2$ |
| 68 | 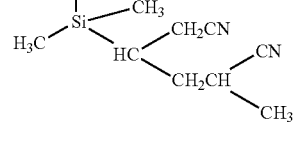<br>68l = C$_9$H$_{15}$N$_2$SiF | 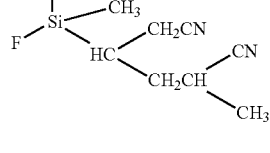<br>68b = C$_8$H$_{12}$N$_2$SiF$_2$ |
|  | 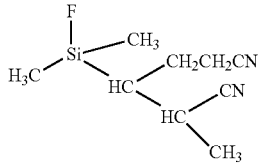<br>68c = C$_9$H$_{15}$N$_2$SiF | 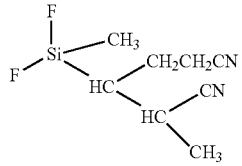<br>68d = C$_8$H$_{12}$N$_2$SiF$_2$ |

TABLE II-continued
| Compound # | Fluorodimethylsilicon Nitrile | Difluoromethylsilicon Nitrile |
|---|---|---|
| 69 | 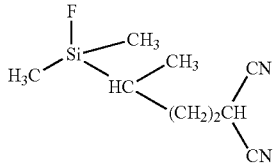 69a = C₉H₁₅N₂SiF | 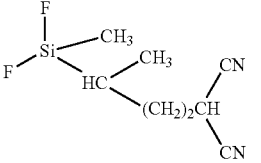 69b = C₈H₁₂N₂SiF₂ |
| | 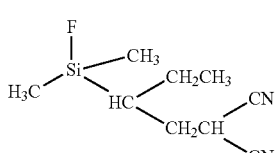 69c = C₉H₁₅N₂SiF | 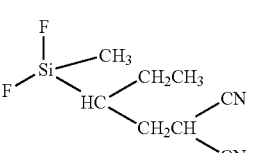 69d = C₈H₁₂N₂SiF₂ |
| 70 | 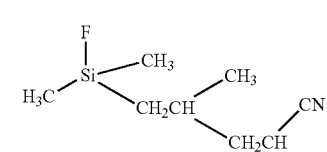 70a = C₉H₁₅N₂SiF | 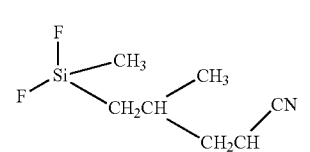 70b = C₈H₁₂N₂SiF₂ |
| | 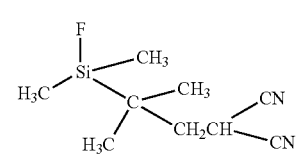 70c = C₉H₁₅N₂SiF | 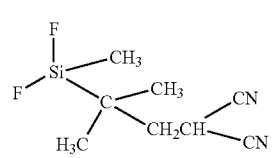 70d = C₈H₁₂N₂SiF₂ |
| 71 | 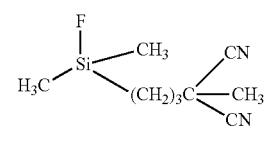 71a = C₉H₁₅N₂SiF | 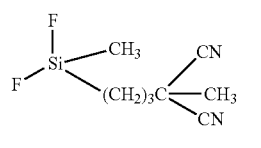 71b = C₈H₁₂N₂SiF₂ |
| | 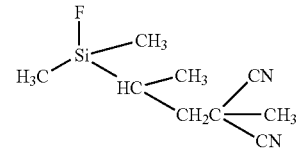 71c = C₉H₁₅N₂SiF | 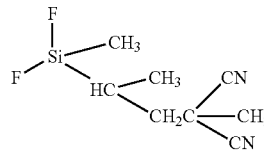 71d = C₈H₁₂N₂SiF₂ |
| 72 | 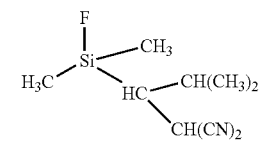 72a = C₉H₁₅N₂SiF | 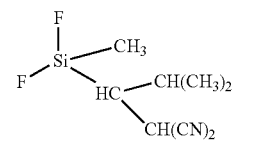 72b = C₈H₁₂N₂SiF₂ |

TABLE II-continued

| Compound # | Fluorodimethylsilicon Nitrile | Difluoromethylsilicon Nitrile |
|---|---|---|
| 73 | $H_3C-Si(F)(CH_3)-(CH_2)_2CH(CH_3)-CH(CN)_2$ <br> 73a = $C_9H_{15}N_2SiF$ | $F-Si(F)(CH_3)-(CH_2)_2CH(CH_3)-CH(CN)_2$ <br> 73b = $C_8H_{12}N_2SiF_2$ |
|  | $H_3C-Si(F)(CH_3)-HC(CH_3)-HC(CH_3)-CH(CN)_2$ <br> 73c = $C_9H_{15}N_2SiF$ | $F-Si(F)(CH_3)-HC(CH_3)-HC(CH_3)-CH(CN)_2$ <br> 73d = $C_8H_{12}N_2SiF_2$ |
| 74 | $H_3C-Si(F)(CH_3)-(CH_2)_4CH(CN)(CN)$ <br> 74a = $C_9H_{15}N_2SiF$ | $F-Si(F)(CH_3)-(CH_2)_4CH(CN)(CN)$ <br> 74b = $C_8H_{12}N_2SiF_2$ |

Also provided by the present invention are methods of making the above-mentioned fluorosilicon nitrile compounds.

In one aspect of the invention, a method is provided which comprises reacting a chlorosilicon nitrile compound with a fluorinating agent under conditions effective to exchange fluorine atoms for the chlorine atoms in the chlorosilicon nitrile compound. The chlorosilicon nitrile compound has a total of four substituents attached to a silicon atom, wherein one or two of the substituents are chlorine atoms, one or two of the substituents are cyanoalkyl groups, which may be the same as or different from each other, and the remainder of the substituents, if any, are alkyl groups, which are the same as or different from each other. The chlorosilicon nitrile compound may correspond to general formula $Si(R^1)(R^2)(R^3)(R^4)$, wherein one or two of $R^1$-$R^4$ are chlorine atoms, one or two of $R^1$-$R^4$ are cyanoalkyl groups, which are the same as or different from each other where two cyanoalkyl groups are present, and the remaining $R^1$-$R^4$, if any, are alkyl groups.

The fluorinating agent may, for example, be selected from the group consisting of HF, MF, $MHF_2$ and $SbF_3$, where M is Na, K, Rb, Cs or $NH_4$. Fluorides of antimony, zinc, lead, mercury, silver, cobalt, copper, tungsten and other metals may be utilized as the fluorinating agent. Sodium fluoroborate may also be used, as can mixtures of $SbF_3$ and $BF_3$ or NaF and sulfuric acid. Other suitable fluorinating agents include neat $BF_3$, $BF_3$ etherates, $Na_2SiF_6$, $NaPF_6$, $NaSbF_6$, $NaBF_4$, $Me_3SnF$, $PF_5$, $PhCBF_4$, $NOBF_4$, and $NO_2BF_4$. If HF (hydrogen fluoride) is employed, it may be used in anhydrous form or in an aqueous-alcoholic or aqueous medium. Potassium hydrogen difluoride and ammonium hydrogen difluoride (ammonium bifluoride) are especially useful fluorinating agents.

Certain of the chlorosilicon nitrile compounds useful as the starting material in the aforementioned fluorination reaction are known compounds that may be prepared using methods known in the art. Such compounds include, for example, compounds having the following CAS registration numbers: 42759-42-2; 59343-99-6; 42759-43-3; 100792-00-5, 1068-40-2; 18243-57-7; 1274903-71-7, 876343-97-4; 2617-09-6; 18276-25-0; 18135-77-8; 103613-06-5; 1071-17-6; 18727-31-6; 7031-17-6; 169206-21-7; 875478-07-2; 161582-95-2; 113641-37-5; and 1186-40-9. Additional chlorosilicon nitrile compounds may be readily synthesized by hydrosilylation of an alkene with a chloroalkylsilane. In one embodiment of such a synthesis, the alkene is a cyanoalkene. The cyanoalkene may suitably be a C3-C10 cyanoalkene, for example, and may contain a single carbon-carbon double bond and one, two or more cyano (—CN) groups per molecule. The structure of the cyanoalkene is selected so as to provide a cyanoalkyl group of the type desired in the fluorosilicon nitrile produced by hydrosilylation. Illustrative examples of suitable cyanoalkenes include, but are not limited to, $CH_3CH=CHCN$ (CAS 4786-20-3); $CH_3C(CN)=CHCN$ (CAS 70240-55-0); $NCCH_2CH=CHCN$ (CAS 7717-24-0); $CH_3CH=C(CN)_2$ (CAS 1508-07-2); $CH_2=C(CN)CH_2CN$ (CAS 24412-94-0); $CH_3CH_2CH=CHCN$ (CAS 13284-42-9); $CH_2=CHCH_2CH_2CN$ (CAS 592-51-8); $CH_3CH=CHCH_2CN$ (CAS 4635-87-4); $CH_3CH=C(CN)CH_3$ (CAS 4403-61-6); $CH_2=C(CN)CH_2CH_3$ (CAS 1647-11-6); $CH_2=C(CH_3)CH_2CN$ (CAS 4786-19-0); $(CH_3)_2C=CHCN$ (CAS 4786-24-7); $CH_2CHCH(CN)CH_3$ (CAS 16529-56-9); $CH_2=C(CH_2CN)CH_2CH_3$ (CAS 1462956-36-0); $CH_2=CHCH(CN)CH_2CH_3$ (CAS 180974-28-1); $CH_2=CHCH_2CH(CN)CH_3$ (CAS 89464-18-6); $CH_3CH_2C(CN)=CHCH_3$ (CAS 89580-25-6); $CH_2CHCH(CH_3)CH_2CN$ (CAS 51980-04-2); $CH_2=CHC(CH_3)_2CN$ (CAS 41405-16-7); $CH_3CH(CN)CH=CHCH_3$ (CAS 37674-624); $CH_2=C(CH_3)CH_2CH_2CN$ (CAS 34998-36-2); $CH_3CH_2CH=CHCH_2CN$ (CAS 16170-44-8); $CH_3CH_2CH_2CH=CHCN$ (CAS 5636-69-1); $CH_2=CHCH_2CH_2CH_2CN$ (CAS 5048-19-1); $(CH_3)_2C=C(CH_3)CN$ (CAS 4786-37-2); $(CH_3)_2C=CHCH_2CN$ (CAS 4786-23-6); $CH_2=C(CN)CH_2CH_2CH_3$ (CAS 3931-57-5); $CH_2=C(CN)CH(CH_3)_2$ (CAS 2813-69-6);

CH$_3$CH$_2$CH$_2$CH=CHCN (CAS 67889-07-0); CH$_2$C(CH$_3$)CH(CN)CH$_3$ (CAS 25653-08-1); (CH$_3$)$_2$CHCH=CHCN (CAS 19124-15-3); CH$_3$CH$_2$C(CH$_3$)=CHCN (CAS 14799-77-0); CH$_3$C(CN)=C(CN)CH$_2$CH$_3$ (CAS 1003003-54-0); NCCH$_2$CH$_2$CH$_2$CH=CHCN (CAS 872307-67-0); CH$_2$=C(CN)CH$_2$CH$_2$CH$_2$CN (CAS 856347-40-5); CH$_3$CH$_2$C(CH$_3$)=C(CN)$_2$ (CAS 13017-50-0); (CH$_3$)$_2$CHCH=C(CN)$_2$ (CAS 13134-03-7); CH$_3$CH=C(CN)CH$_2$CH$_2$CN (CAS 22485-88-7); CH$_2$=C(CN)CH$_2$CH(CN)CH$_3$ (CAS 35299-21-9); CH$_2$=CHCH$_2$CH(CN)CH$_2$CN (CAS 364453-09-5); CH$_3$CH=CHCH(CN)CH$_2$CN (CAS 36453-10-8); CH$_3$CH$_2$CH=C(CN)CH$_2$CN (CAS 36453-11-9); (CH$_3$)$_2$C=C(CN)CH$_2$CN (CAS 67386-03-2); NCCH$_2$C(CH$_3$)=CHCH$_2$CN (CAS 76257-96-0); CH$_2$=C(CH$_2$CN)CH$_2$CH$_2$CN (CAS 80718-20-3); CH$_2$=C(CH$_2$CN)CH(CN)CH$_3$ (CAS 80718-26-9); CH$_3$CH$_2$CH$_2$CH=C(CN)$_2$ (CAS 87948-15-0); CH$_3$CH(CN)CH=CHCH$_2$CN (CAS 122917-04-8); (NC)$_2$CHCH$_2$CH=CHCH$_3$ (CAS 130575-29-0); CH$_2$=C(CH$_3$)CH$_2$CH(CN)$_2$ (CAS 145050-18-6); CH$_2$=CHCH$_2$C(CN)$_2$CH$_3$ (CAS 154657-02-0); (CH$_3$)$_2$C=CHCH(CN)$_2$ (CAS 442661-894); CH$_2$=CHCH(CH$_3$)CH(CN)$_2$ (CAS 443124-95-6); and CH$_2$=CHCH$_2$CH$_2$CH(CN)$_2$ (CAS 475197-78-5).

The chloroalkylsilane may be a silane containing, as substituents attached to the silicon atom, one or two hydrogen atoms, one chlorine atom and one or two alkyl groups, which may be the same as each other or different from each other. Where one hydrogen atom is present, one molecule of cyanoalkene reacts with one molecule of chloroalkylsilane in the hydrosilylation reaction, thereby introducing a single cyanoalkyl group into the silane. When two hydrogen atoms are present, two molecules of cyanoalkene react with one molecule of chloroalkylsilane, thereby introducing two cyanoalkyl groups into the silane. In this embodiment, the chloroalkyl silane may correspond to the general structure SiCl(H)$_m$(R)$_{3-n}$, where n is 1 or 2 and R is alkyl. In another aspect of the invention, the chloroalkyl silane may be a silane containing, as substituents attached to the silicon atom, one or two hydrogen atoms, two chlorine atoms, and, where only one hydrogen atom is attached to silicon, a single alkyl group. In this embodiment, the chloroalkyl silane may correspond to the general structure SiCl$_2$(H)$_n$(R)$_{2-n}$, where n is 1 or 2 and R, if present, is alkyl. Where one hydrogen atom is present, one molecule of cyanoalkene reacts with one molecule of ehloroalkylsitane in the hydrosilylation reaction, thereby introducing a single cyanoalkyl group into the silane. When two hydrogen atoms are present, two molecules of alkene react with one molecule of chloroalkylsilane, thereby introducing two cyanoalkyl groups into the silane.

The alkyl groups may, for example, be a C1-C8 alkyl group such as methyl, ethyl, n-propyl, isopropyl, n-butyl and isomers thereof, n-pentyl and isomers thereof, n-hexyl and isomers thereof, n-heptyl and isomers thereof, n-octyl and isomers thereof and combinations of such alkyl groups. The chloroalkylsilane thus may correspond to the general formula HSi(R$^1$)(R$^2$)(R$^3$), wherein one or two of R$^1$-R$^3$ are chlorine atoms and the remaining R$^1$-R$^3$ are alkyl groups, which may be the same as or different from each other where more than one alkyl group per molecule is present.

An example of such a synthetic reaction scheme is shown below. In this example, the alkene 2-cyanobut-1-ene (CAS #1647-11-6) is hydrosilylated with chlorodimethylsilane (CDMS), leading to a chlorosilicon nitrite having the structure shown (Reaction 1A). The chlorosilicon nitrite is then reacted with a fluorinating agent to produce fluorosilicon nitrite compound 30a having the structure shown (Reaction 1B).

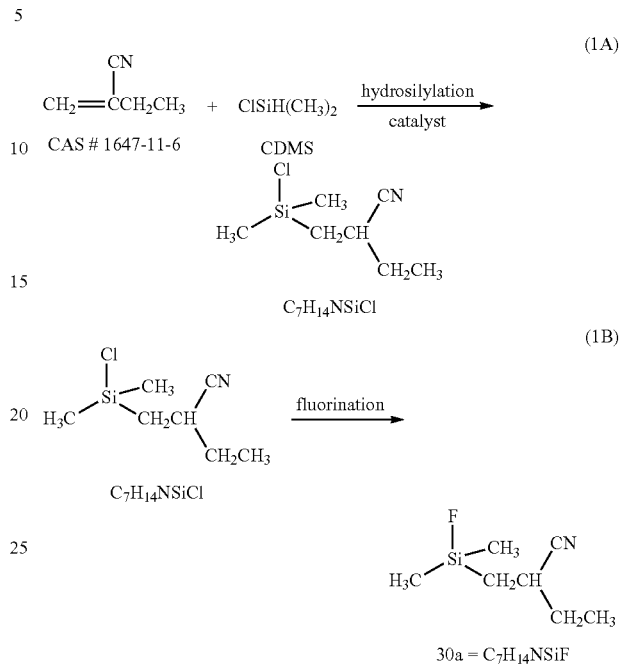

A further method of making a fluorosilicon nitrite compound in accordance with the present invention comprises hydrosilylation of an alkene with a fluoroalkylsilane (i.e., reacting the alkene and fluoroalkylsilane under hydrosilylation conditions). The reacted alkene may be a cyanoalkene, for example. Suitable cyanoalkenes include any of the previously mentioned cyanoalkenes.

The fluoroalkylsilane may be a silane containing, as substituents attached to the silicon atom, one or two hydrogen atoms, one fluorine atom and one or two alkyl groups, which may be the same as each other or different from each other. The total number of hydrogen atoms, fluorine atom, and alkyl groups equals four. Where one hydrogen atom attached to silicon is present, one molecule of cyanoalkene reacts with one molecule of fluoroalkylsilane in the hydrosilylation reaction, thereby introducing a single cyanoalkyl group into the silane. When two hydrogen atoms attached to silicon are present, two molecules of cyanoalkene react with one molecule of fluoroalkylsilane, thereby introducing two cyanoalkyl groups into the silane. In this embodiment, the fluoroalkyl silane may correspond to the general structure SiF(H)$_n$(R)$^{3-n}$, where n is 1 or 2 and R is alkyl. In another aspect of the invention, the fluoroalkyl silane may be a slime containing, as substituents attached to the silicon atom, one or two hydrogen atoms, two fluorine atoms, and, where only one hydrogen atom is attached to silicon, a single alkyl group. The total number of hydrogen atoms, fluorine atoms and alkyl group equals four. In this embodiment, the fluoroalkyl silane may correspond to the general structure SiF$_2$(H)$_n$(R)$_{2-n}$, where n is 1 or 2 and R, if present, is alkyl. Where one hydrogen atom attached to silicon is present, one molecule of cyanoalkene reacts with one molecule of fluoroalkylsilane in the hydrosilylation reaction, thereby introducing a single cyanoalkyl group into the silane. When two hydrogen atoms attached to silicon are present, two molecules of cyanoalkene react with one molecule of fluoroalkylsilane, thereby introducing two cyanoalkyl groups into the silane.

The alkyl groups may, for example, be a C1-C8 alkyl group such as methyl, ethyl, n-propyl, isopropyl, n-butyl and isomers thereof, n-pentyl and isomers thereof, n-hexyl and isomers thereof, n-heptyl and isomers thereof, n-octyl and isomers thereof and combinations of such alkyl groups.

The fluoroalkylsilane thus may correspond to the general formula $HSi(R^1)(R^2)(R^3)$, wherein one or two of $R^1$-$R^3$ are fluorine atoms and the remaining $R^1$-$R^3$ are alkyl groups, which may be the same as or different from each other where more than one alkyl group per molecule is present.

The following reaction scheme (Reaction 1C) is an example of such a reaction. In this example, fluorosilicon nitrile compound 30a is prepared by direct hydrosilylation of the alkene 2-cyanobut-1-ene with fluorodimethylsilane (FDMS).

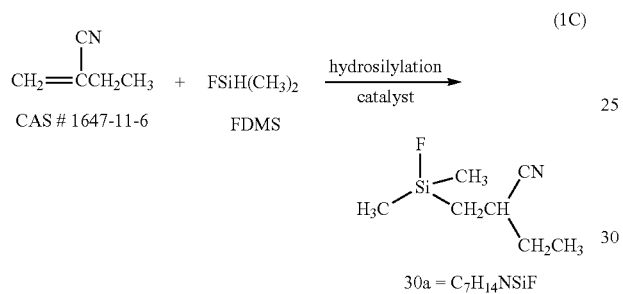

In one embodiment of the invention, the above-mentioned hydrosilylation reactions are carried out in the presence of a hydrosilylation catalyst, in particular an organoplatinum coordination complex having activity as a hydrosilylation catalyst. Karstedt's catalyst, which is an organoplatinum compound derived from divinyl-containing disiloxane (by treatment of chloroplatinic acid with divinyltetramethyldisiloxane), is an example of a suitable catalyst for this purpose. Other suitable hydrosilylation catalysts include, for example, Wilkinson's catalyst (tris(triphenylphosphone)rhodium (I) chloride), the cobalt carbonyl complex $Co_2(CO)_8$, and $H_2PtCl_6$(Speier's catalyst). Hydrosilylation typically proceeds in an anti-Markovnikov manner. However, depending upon the reaction conditions used, hydrosilylation may not be completely selective; that is, a mixture of isomeric hydrosilylation products may be obtained. The individual components of such reaction product mixtures may be purified and isolated using any conventionally known techniques, such as fractional distillation. Alternatively, the mixture of components may be utilized for the desired end use without such fractionation or separation.

Typically, where it is desired to introduce a single cyanoalkyl group into a silane, the molar ratio of cyanoalkene to fluoroalkylsilane may be approximately 1:1, e.g., from about 0.7:1 to about 1.3:1. If it is desired to introduce two cyanoalkyl groups, the molar ratio of cyanoalkene to fluoroalkylsilane may be approximately 2:1, e.g., from about 1.5:1 to about 15:1. The hydrosilylation may be carried out using an organic solvent, e.g., an aromatic hydrocarbon, as a reaction medium. The mixture of cyanoalkene, fluoroalkylsilane, hydrosilylation catalyst and optional solvent may be heated for a time and at a temperature effective to provide the desired conversion of the starting materials. For example, reaction temperatures of from about 50° C. to about 110° C. and reaction times of from about 1 to about 6 hours may be utilized.

Aspects of the present invention include:
1. A fluorosilicon nitrile compound having a total of four substituents attached to a silicon atom, wherein one or two of the substituents are fluorine atoms, one or two of the substituents are cyanoalkyl groups, which are the same as or different from each other, and the remainder of the substituents, if any, are alkyl groups, which are the same as or different from each other;
   subject to the proviso that the fluorosilicon nitrile compound is not $SiF_2(CH_3)(CH_2CH_2CH(CN)CH_3)$; $SiF_2(CH_3)(CH_2CH_2CH_2CN)$; $SiF_2(CH_3)(CH_2CH(CH_3)CH_2CN)$; or $SiF_2[CH_2CH(CH_3)CH_2CN]_2$.
2. The fluorosilicon nitrile compound of claim 1, wherein one substitutent is a fluorine atom, one substituent is a cyanoalkyl group, and two substituents are alkyl groups, which are the same as or different from each other.
3. The fluorosilicon nitrite compound of claim 1, wherein two substituents are fluorine atoms, one substituent is a cyanoalkyl group, and one substituent is an alkyl group.
4. The fluorosilicon nitrile compound of claim 1, wherein one substituent is a fluorine atom, two substituents are cyanoalkyl groups, which are the same as or different from each other, and one substituent is an alkyl group.
5. The fluorosilicon nitrile compound of claim 1, wherein two substituents are fluorine atoms and two substituents are cyanoalkyl groups, which are the same as or different from each other.
6. The fluorosilicon nitrite compound of any one of the preceding claims, wherein the cyanoalkyl groups are C2-C9 cyanoalkyl groups.
7. The fluorosilicon nitrile compound of claim 1, wherein at least one alkyl group is present and the alkyl group is a C1-C8 alkyl group,
8. The fluorosilicon nitrite compound of any one of the preceding claims, wherein the cyanoalkyl group or cyanoalkyl groups contain(s) a single cyano group per cyanoalkyl group.
9. The fluorosilicon nitrite compound of any one of claims 1 through 7, wherein the cyanoalkyl group or cyanoalkyl groups contain(s) two cyano groups per cyanoalkyl group.
10. The fluorosilicon nitrite compound of any one of the preceding wherein the cyanoalkyl group or cyanoalkyl groups contain(s) a cyano group which is substituted at a terminal position of an alkyl radical.
11. The fluorosilicon nitrite compound of any one of the preceding wherein the cyanoalkyl group or cyanoalkyl groups contain(s) a cyano group which is substituted at an internal position of an alkyl radical.
12. The fluorosilicon nitrite compound of any one of the preceding claims, wherein the cyanoalkyl group or cyanoalkyl groups are selected from the group consisting of:
    —$CH_2CH(CN)CH_3$;
    —$CH(CN)CH_2CH_3$;
    —$C(CN)(CH_3)_2$;
    —$CH_2CH_2CN$;
    —$CH(CN)CH_3$;
    —$CH_2CH_2CH(CN)CH_3$;
    —$CH_2CH(CN)CH_2CH_3$;
    —$(CH_2)_3CN$;
    —$(CH_2)_2CN$;
    —$(CH_2)_4CN$;

—(CH$_2$)$_5$CN;
—(CH$_2$)$_3$C(CN)$_2$CH$_3$;
—CH(CH$_3$)CH$_2$CN;
—CH(CN)CH(CN)CH$_3$;
—C(CN)(CH$_3$)CH$_2$CN;
—CH(CH$_2$CN)$_2$;
—CH(CN)CH$_2$CH$_2$CN;
—CH(CH$_3$)CH(CN)$_2$;
—C(CN)$_2$(CH$_2$CH$_3$);
—CH$_2$CH(CN)CH$_2$CN;
—C(CN)(CH$_3$)CH$_2$CN;
—CH(CH$_2$CH$_3$)CH$_2$CN;
—CH(CN)CH$_2$CH$_2$CH$_3$;
—CH(CH$_3$)CH$_2$CH$_2$CN;
—CH(CH$_2$CN)CH$_2$CH$_3$;
—CH(CH$_3$)CH(CN)CH$_3$;
—C(CN)(CH$_3$)CH$_2$CH$_3$;
—CH$_2$CH(CH$_3$)CH$_2$CN;
—C(CH$_3$)$_2$CH$_2$CN;
—CH(CN)CH(CH$_3$)$_2$;
—CH$_2$CH$_2$CH(CN)CH$_3$;
—CH$_2$CH(CH$_2$CN)CH$_2$CH$_3$;
—C(CH$_3$)(CH$_2$CH$_3$)CH$_2$CN;
—CH$_2$CH$_2$CH(CN)CH$_2$CH$_3$;
—CH(CH$_3$)CH(CN)CH$_2$CH$_3$;
—CH$_2$CH$_2$CH$_2$CH(CN)CH$_3$;
—CH(CH$_3$)(CH$_2$CH(CN)CH$_3$;
—C(CH$_2$CH$_3$)$_2$(CN);
—CH$_2$CH$_2$CH(CH$_3$)CH$_2$CN;
—CH(CH$_3$)CH(CH$_3$)CH$_2$CN;
—(CH$_2$)$_2$C(CH$_3$)$_2$CN;
—CH(CH$_3$)C(CH$_3$)$_2$CN;
—CH(CH$_2$CH$_3$)CH(CN)CH$_3$;
—CH$_2$CH(CH$_3$)CH$_2$CH$_2$CN;
—C(CH$_3$)$_2$CH$_2$CH$_2$CN;
—CH(CH$_2$CH$_3$)CH$_2$CH$_2$CN;
—CH(CH$_2$CN)CH$_2$CH$_2$CH$_3$;
—CH(CN)CH$_2$CH$_2$CH$_2$CH$_3$;
—CH(CH$_3$)CH$_2$CH$_2$CH$_2$CN;
—C(CH$_3$)$_2$CH(CN)CH$_3$;
—C(CH$_3$)(CN)CH(CH$_3$)$_2$;
—CH(CH$_2$CN)CH(CH$_3$)$_2$;
—CH$_2$CH(CN)CH$_2$CH$_2$CH$_3$;
—C(CH$_3$(CN)CH$_2$CH$_2$CH$_3$;
—CH$_2$CH(CN)CH(CH$_3$)$_2$;
—CH(CN)CH$_2$CH$_2$CH$_2$CH$_3$;
—CH$_2$CH(CH$_3$)CH(CN)CH$_3$;
—CH(CN)CH$_2$CH(CH$_3$)$_2$;
—CH(CN)CH(CH$_3$)CH$_2$CH$_3$;
—C(CH$_3$)(CN)CH(CN)CH$_2$CH$_3$;
—C(CN)(CH$_2$CH$_3$)CH(CN)CH$_3$;
—CH(CH$_2$CN)CH$_2$CH$_2$CH$_2$CN;
—CH(CN)CH$_2$CH$_2$CH$_2$CN;
—CH$_2$CH(CN)CH$_2$CH$_2$CN;
—C(CH$_3$)(CN)CH$_2$CH$_2$CH$_2$CN;
—C(CH$_3$)(CH$_2$CH$_3$)CH(CN)$_2$;
—C(CN)$_2$CH(CH$_3$)CH$_2$CH$_3$;
—C(CN)$_2$CH$_2$CH(CH$_3$)$_2$;
—CH(CH(CN)$_2$)CH(CH$_3$)$_2$;
—C(CN)(CH$_2$CH$_3$)CH$_2$CH$_2$CN;
—CH(CH$_3$)CH(CN)CH$_2$CH$_2$CN;
—CH$_2$CH(CN)CH$_2$CH(CN)CH$_3$;
—C(CN)(CH$_3$)CH$_2$CH(CN)CH$_3$;
—(CH$_2$)$_3$CH(CN)CH$_2$CN;
—CH(CH$_3$)CH$_2$CH(CN)CH$_2$CN;
—CH(CH$_2$CH$_3$)CH$_2$CH(CN)CH$_2$CN;
—C(CN)(CH$_2$CN)CH$_2$CH$_2$CH$_3$;

—C(CH$_3$)$_2$CH(CN)CH$_2$CN;
—C(CN)(CH$_2$CN)CH(CH$_3$)$_2$;
—C(CH$_3$)(CH$_2$CN)CH$_2$CH$_2$CN;
—CH(CH$_2$CN)CH(CH$_3$)CH$_2$CN;
—CH$_2$CH(CH$_2$CN)CH$_2$CH$_2$CN;
—CH$_2$CH(CH$_2$CN)CH(CN)CH$_3$;
—C(CH$_3$)(CH$_2$CN)CH(CN)CH$_3$;
—CH(CH(CN)$_2$)CH$_2$CH$_2$CH$_3$;
—C(CN)$_2$CH$_2$CH$_2$CH$_2$CH$_3$;
—CH(CH$_2$CN)CH$_2$CH(CN)CH$_3$;
—CH(CH$_2$CH$_2$CN)CH(CN)CH$_3$;
—CH(CH$_3$)CH$_2$CH$_2$CH(CN)$_2$;
—CH(CH$_2$CH$_3$)CH$_2$CH(CN)$_2$;
—CH$_2$CH(CH$_3$)CH$_2$CH(CN)$_2$;
—C(CH$_3$)$_2$CH$_2$CH(CN)$_2$;
—CH$_2$CH$_2$CH$_2$C(CN)$_2$CH$_3$;
—CH(CH$_3$)CH$_2$C(CN)$_2$CH$_3$;
—CH(CH(CN)$_2$)CH(CH$_3$)$_2$;
—CH$_2$CH$_2$CH(CH$_3$)CH(CN)$_2$;
—CH(CH$_3$)CH(CH$_3$)CH(CN)$_2$; and
—CH$_2$CH$_2$CH$_2$CH$_2$CH(CN)$_2$ and combinations thereof.

13. The fluorosilicon nitrile compound of claim 12, wherein the fluorosilicon nitrile compound contains, as substituents attached to the silicon atom, one fluorine atom, one cyanoalkyl group, and two C1-C8 alkyl groups, which are the same as or different from each other.

14. The fluorosilicon nitrile compound of claim 13, wherein the fluorosilicon nitrile compound contains, as substituents attached to the silicon atom, two alkyl groups selected from the group consisting of methyl, ethyl, n-propyl, iso-propyl, n-butyl, sec-butyl, iso-butyl, tert-butyl and combinations thereof.

15. The fluorosilicon nitrile compound of claim 12, wherein the fluorosilicon nitrile compound contains, as substituents attached to the silicon atom, two fluorine atoms, one cyanoalkyl group and one C1-C8 alkyl group.

16. The fluorosilicon nitrile compound of claim 12 or 15, wherein the fluorosilicon nitrile compound contains, as substituents attached to the silicon atom, two alkyl groups selected from the group consisting of methyl, ethyl, n-propyl, iso-propyl, n-butyl, sec-butyl, iso-butyl, tert-butyl and combinations thereof.

17. A fluorosilicon nitrile compound of general formula Si(R$^1$)(R$^2$)(R$^3$)(R$^4$), wherein one or two of R$^1$-R$^4$ are fluorine atoms, one or two of R$^1$-R$^4$ are cyanoalkyl groups, which are the same as or different from each other where two cyanoalkyl groups are present, and the remaining R$^1$-R$^4$, if any, are alkyl groups; subject to the proviso that the fluorosilicon nitrile compound is not SiF$_2$(CH$_3$)(CH$_2$CH$_2$CH(CN)CH$_3$; SiF$_2$(CH$_3$)(CH$_2$CH$_2$CH$_2$CN); SiF$_2$(CH$_3$)(CH$_2$CH(CH$_3$)CH$_2$CN); or SiF$_2$[CH$_2$CH(CH$_3$)CH$_2$CN]$_2$.

18. A method of making a fluorosilicon nitrile compound in accordance with any one of the preceding claims, wherein the method comprises reacting a chlorosilicon nitrile compound with a fluorinating agent under conditions effective to exchange fluorine atoms for the chlorine atoms in the chlorosilicon nitrile compound and wherein the chlorosilicon nitrile compound has a total of four substituents attached to a silicon atom, wherein one or two of the substituents are chlorine atoms, one or two of the substituents are cyanoalkyl groups, which may be the same as or different from each other, and the remainder of the substituents, if any, are alkyl groups, which are the same as or different from each other.

19. The method of claim 18, wherein the fluorinating agent is selected from the group consisting of HF, MF, $MHF_2$ and $SbF_3$, where M is Na, K, Rb, Cs or $NH_4$.

20. The method of claim 18 or 19, wherein the chlorosilicon nitrile compound is prepared by hydrosilylation of an alkene with a chloroalkylsilane.

21. The method of claims 18 through 20, wherein the alkene is a cyanoalkene.

22. A method of making a fluorosilicon nitrile compound in accordance with any one of the preceding claims, wherein the method comprises hydrosilylation of an alkene with a fluoroalkylsilane.

23. The method of claim 22, wherein the alkene is a cyanoalkene.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein.

What is claimed is:

1. A method of making a fluorosilicon nitrile compound comprising reacting a chlorosilicon nitrile compound with a fluorinating agent selected from the group consisting of HF, MF, $MHF_2$ where M is Na, K, Rb, Cs or $NH_4$, $SbF_3$, $ZnF_2$, $PbF_2$, $Hg_2F_2$, $AgF_2$, $CoF_2$, $CuF_2$, $WF_6$, $NaBF_4$, mixtures of NaF and $H_2SO_4$, $BF_3$, $BF_3$ etherates, $Na_2SiF_6$, $NaPF_6$, $NaSbF_6$, $NaBF_4$, $Me_3SnF$, $PF_5$, $PhCBF_4$, $NOBF_4$, $NO_2BF_4$, $KHF_2$, $NH_4HF_2$ under conditions effective to exchange fluorine atoms for the chlorine atoms in the chlorosilicon nitrile compound and wherein the chlorosilicon nitrile compound has a total of four substituents attached to a silicon atom, wherein one or two of the substituents are chlorine atoms, one or two of the substituents are cyanoalkyl groups, which may be the same as or different from each other, and the remainder of the substituents, if any, are alkyl groups, which are the same as or different from each other.

2. The method of claim 1, wherein the chlorosilicon nitrile compound is prepared by hydrosilylation of an alkene with a chloroalkylsilane.

3. The method of claim 2, wherein the alkene is a cyanoalkene.

* * * * *